United States Patent [19]
Koyfman et al.

[11] Patent Number: 5,370,031
[45] Date of Patent: Dec. 6, 1994

[54] BRAIDER APPARATUS WITH IMPROVED BOBBIN HOLDER

[75] Inventors: Ilya Koyfman, Orange, Conn.; Josep Serra, Barcelona, Spain; Michael P. Chesterfield, Norwalk, Conn.

[73] Assignee: United States Surgical Corporation, Norwalk, Conn.

[21] Appl. No.: 48,932

[22] Filed: Apr. 15, 1993

Related U.S. Application Data

[63] Continuation of Ser. No. 605,554, Oct. 30, 1990, abandoned, which is a continuation-in-part of Ser. No. 569,079, Aug. 17, 1990, abandoned.

[51] Int. Cl.$^5$ .......................... D04C 3/14; D04C 3/48
[52] U.S. Cl. .................................. 87/55; 87/54; 87/56; 87/61; 87/62
[58] Field of Search ................. 87/20, 21, 22, 54, 55, 87/56, 57, 61, 62

[56] References Cited

U.S. PATENT DOCUMENTS

| | | |
|---|---|---|
| 776,842 | 12/1904 | Horwood . |
| 998,031 | 7/1911 | Neufeld ................. 87/22 |
| 1,154,964 | 9/1915 | Bentley . |
| 1,285,451 | 11/1918 | Stanton . |
| 1,358,173 | 11/1920 | Penso et al. . |
| 1,442,432 | 1/1923 | Hooper . |
| 1,486,527 | 3/1924 | Larkin . |
| 1,582,055 | 4/1926 | Krissiep . |
| 1,633,346 | 6/1927 | Mossberg ................. 87/22 |
| 1,765,117 | 6/1930 | Wright et al. . |
| 1,785,683 | 12/1930 | Mallory . |
| 1,997,210 | 4/1935 | Ford et al. . |
| 2,053,161 | 9/1936 | Olson et al. ................. 87/56 |
| 2,079,836 | 5/1937 | Brown et al. . |
| 2,200,323 | 5/1940 | Barrans et al. . |
| 2,337,770 | 12/1943 | Rickenbacher . |
| 2,452,136 | 10/1948 | Marti . |
| 2,895,371 | 7/1959 | Herzog . |
| 2,897,715 | 8/1959 | Olson ................. 87/56 |
| 2,897,716 | 8/1959 | Olson ................. 87/57 |
| 2,986,061 | 5/1961 | Carter ................. 87/56 |

(List continued on next page.)

FOREIGN PATENT DOCUMENTS

| | | |
|---|---|---|
| 423412 | 4/1911 | France . |
| 2482634 | 11/1981 | France . |
| 1660004 | 6/1971 | Germany . |
| 2162170 | 6/1973 | Germany . |
| 1785682 | 3/1975 | Germany . |
| 3038343 | 5/1982 | Germany . |
| 3144589 | 5/1983 | Germany . |
| 3412998 | 10/1985 | Germany . |
| 85215 | 6/1920 | Switzerland . |
| 138069 | 9/1920 | United Kingdom . |
| 375654 | 6/1932 | United Kingdom ................ 87/22 |
| 579402 | 8/1946 | United Kingdom . |
| 836240 | 6/1960 | United Kingdom . |
| 871835 | 7/1961 | United Kingdom ................ 87/56 |
| 872679 | 7/1961 | United Kingdom . |
| 1332591 | 10/1973 | United Kingdom . |
| 1555941 | 11/1979 | United Kingdom . |
| 2081756 | 2/1982 | United Kingdom . |

(List continued on next page.)

OTHER PUBLICATIONS

Published Description on Ratera Braiding Machine, No Date Available.

*Primary Examiner*—Daniel P. Stodola
*Assistant Examiner*—William Stryjewski

[57] ABSTRACT

An apparatus is disclosed for braiding fine denier yarns to form a braided suture product which includes a carrier housing, a main carrier support plate for guiding a plurality of yarn carriers through predetermined paths while dispensing fine denier yarns toward a braiding zone. Each yarn carrier has a spindle for mounting a molded bobbin, with a spindle tip having a recess engageable with resilient leg portions of a bobbin hold down member hingedly mounted for rotation relative to the carrier housing. Tension on the yarn controls rotational movement of the bobbin to dispense yarn therefrom, and the tension of the final braided suture product is controlled to form a product of predetermined uniform appearance.

39 Claims, 12 Drawing Sheets

U.S. PATENT DOCUMENTS

| | | | |
|---|---|---|---|
| 3,004,463 | 10/1961 | Griesemer | 87/56 |
| 3,038,367 | 6/1962 | Karg et al. | |
| 3,045,526 | 7/1962 | Harris | |
| 3,187,752 | 6/1965 | Glick | 128/335.5 |
| 3,362,283 | 1/1968 | Dergachev et al. | |
| 3,363,502 | 1/1968 | Florentine et al. | |
| 3,396,625 | 8/1968 | Faulkner | 87/22 |
| 3,565,077 | 2/1971 | Glick | 128/335.5 |
| 3,783,736 | 1/1974 | Richardson | |
| 3,817,147 | 6/1974 | Richardson | |
| 3,854,375 | 12/1974 | Lefevre | |
| 4,014,973 | 3/1977 | Thompson | 264/290 R |
| 4,034,643 | 7/1977 | Iannucci et al. | |
| 4,043,344 | 8/1977 | Landi et al. | 128/335.5 |
| 4,047,533 | 9/1977 | Perciaccente et al. | 128/335.5 |
| 4,084,479 | 4/1978 | Ratera | |
| 4,158,984 | 6/1979 | Griffiths | |
| 4,304,169 | 12/1981 | Cimprich et al. | |
| 4,333,380 | 6/1982 | Kozlowski | |
| 4,574,679 | 3/1986 | Lasher | |
| 4,716,807 | 1/1988 | Fischer | |
| 4,736,668 | 4/1988 | Moyer | |
| 4,753,149 | 6/1988 | Celani | |
| 4,765,220 | 8/1988 | Iannucci et al. | |
| 4,785,709 | 11/1988 | Freitas | |
| 4,802,398 | 2/1989 | Champlin et al. | |
| 4,909,127 | 3/1990 | Skelton et al. | |
| 4,922,798 | 5/1990 | Ivsan et al. | |
| 4,959,069 | 9/1990 | Brennan et al. | 606/228 |
| 5,019,093 | 5/1991 | Kaplan et al. | 606/228 |
| 5,059,213 | 10/1991 | Chesterfield et al. | 606/228 |
| 5,181,923 | 1/1993 | Chesterfield et al. | 606/228 |

FOREIGN PATENT DOCUMENTS

| | | | |
|---|---|---|---|
| 283477 | 12/1970 | U.S.S.R. | |
| 255802 | 5/1976 | U.S.S.R. | |
| 524872 | 11/1976 | U.S.S.R. | |
| 800259 | 1/1981 | U.S.S.R. | 87/57 |

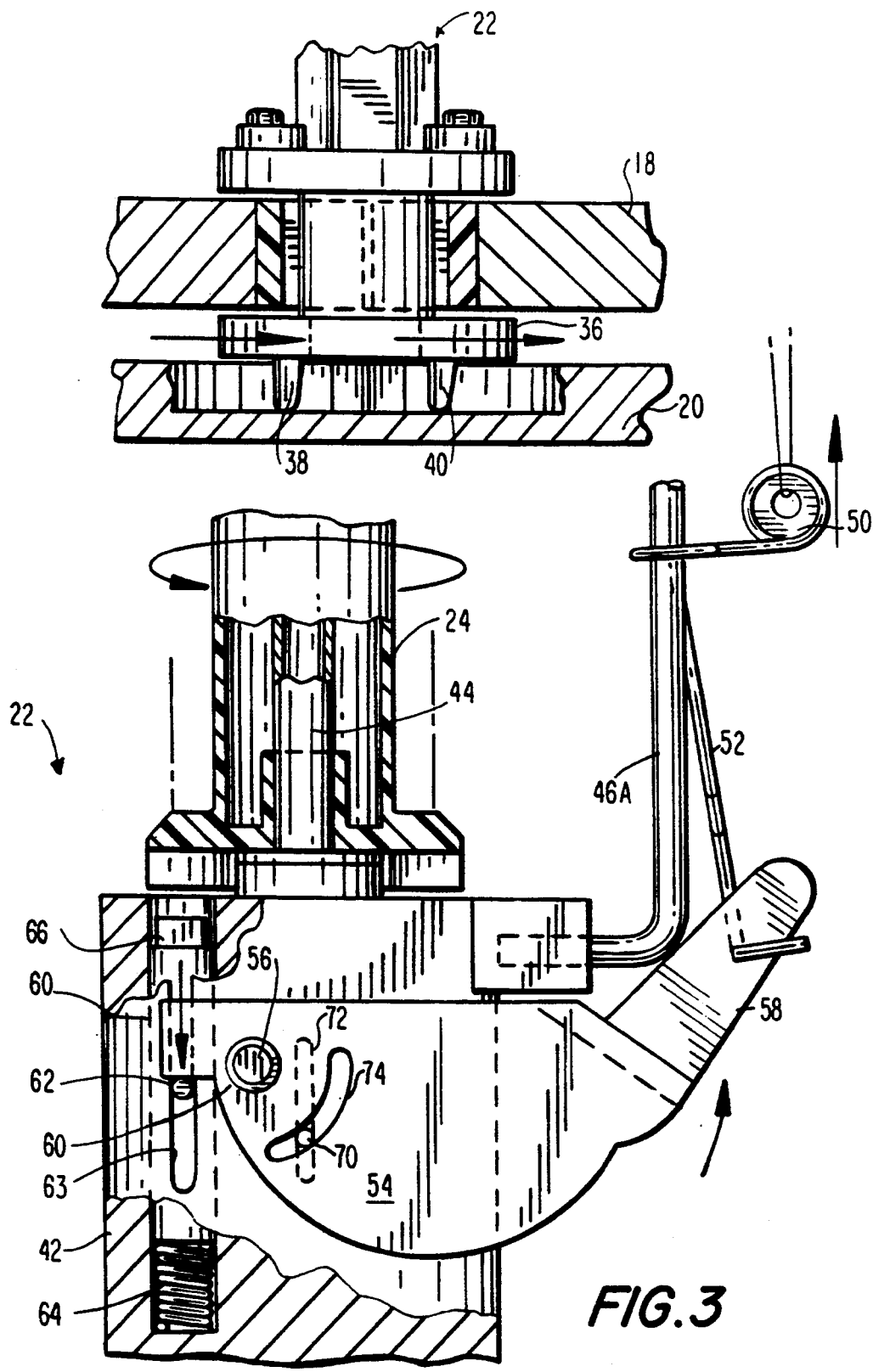

BRAIDER APPARATUS WITH IMPROVED BOBBIN HOLDER

This application is a continuation of copending application Ser. No. 07/605,554 filed on Oct. 30, 1990, now abandoned, which is a continuation-in-part of application Ser. No. 07/569,079 filed Aug. 17, 1990.

TECHNICAL FIELD

The present invention relates to a device for braiding fine denier yarns and, more particularly, to an improved braider bobbin top holder particularly suited for use with a device for braiding fine denier yarns to make surgical sutures.

BACKGROUND OF THE INVENTION

Braided products and apparatus for production of such products are well-knows. Typical of the braiding mechanisms used for such products are disclosed in U.S. Pat. Nos. 776,842 to Horwood, 1,154,964 to Bentley, 1,285,451 to Stanton, 1,358,173 to Penso et al., 1,486,527 to Larkin, 1,785,683 to Mallory, 2,079,836 to Brown et al., 2,200,323 to Barrans et al., 2,452,136 to Marti, 4,158,984 to Griffiths, 4,304,169 to Cimprich et al., 4,333,380 to Kozlowski, 4,716,807 to Fischer, 4,753,149 to Celani, 4,909,127 to Skelton et al. and 4,922,798 to Ivsan. British Patent Publication No. 138,069 dated Sep. 2, 1920 relates to improvements in such braiding devices.

Sutures intended for the repair of body tissues must meet certain requirements: they must be substantially non-toxic, capable of being readily sterilized, they must have good tensile strength and have acceptable knot-tying and knot-holding characteristics and if the sutures are of the bio-absorbable variety, the bio-absorption of the suture must be closely controlled.

Sutures have been constructed from a wide variety of materials including surgical gut, silk, cotton, polyolefins such as polypropylene, polyamides, polyesters such as polyethylene terephthalate, polyglycolic acid, glycolide-lactide copolymer, etc. Although the optimum structure of a suture is that of a monofilament, since certain materials of construction would provide a stiff monofilament suture lacking acceptable handling, knot-tying and knot-holding properties, sutures manufactured from such materials have been provided as braided structures. Thus, for example, sutures manufactured from silk, polyamide, polyester and bio-absorbable glycolide-lactide copolymer are usually provided as multifilament braids.

currently available braided suture products are braided on conventional braider apparatus having yarn bobbin carriers which travel around the perimeter of a braider deck to result in a tubular type braid with the yarns crossing over each other on the surface of the braid. In larger suture sizes, e.g., 5/0 and larger, the tubular braid, or sheath, is constructed about a core structure which is fed through the center of the braider. Known tubular braided sutures, including those possessing cores, are disclosed, e.g., in U.S. Pat. Nos. 3,187,752; 3,565,077; 4,014,973; 4,043,344; and 4,047,533.

Recent attempts to improve the flexibility, hand and tissue drag characteristics of braided sutures have resulted in new braid structures possessing a significantly greater number of sheath yarns for a given overall denier, the sheath yarns being fabricated from individual filaments of finer denier than filaments which are typical of known types of braided sutures. Braided sutures of this type are disclosed and claimed in U.S. patent application Ser. No. 491,215 filed Mar. 9, 1990 now U.S. Pat. No. 5,019,093 on May 28, 1991, and related applications. The foregoing application discloses sutures braided from yarns having a denier in the range of about 0.2 to 6.0 and, optionally, a core having a denier of from about 50 to about 2500 denier. Improvements in such apparatus and methods for continuously braiding fine denier yarns into fine braided products having predetermined construction and appearance suitable for use in body tissue repair are disclosed in parent application Ser. No. 07/569,079, now abandoned in favor of FWC application Ser. No. 08/702,344, incorporated herein by reference, and include a quick release braider bobbin top holder. The foregoing improvements and those of the present application may find application in the manufacture of both tubular braided structures and so-called spiroid braided structures, with or without a core.

SUMMARY OF THE INVENTION

The present invention relates to an improved apparatus for braiding elongate flexible members to form a final braided product, preferably a surgical suture made from fine denier yarns. The braided product may be of the type formed only of a tubular braided sheath, a substantially solid spiroid braid, or a tubular or spiroid braided sheath formed about a center core. In particular, the present invention is directed to improvements which make it possible to quickly mount and/or remove a yarn bobbin onto or from a yarn bobbin carrier with high efficiency and speed and to secure the bobbin to the carrier with a securing mechanism which is simple to operate, does not require a high level of dexterity, and which is not tiring or injurious to the muscles of the operator.

In the braider apparatus of the present invention a plurality of yarn bobbin carriers move about a main carrier support plate to dispense yarns toward a braiding zone where the yarns are braided together to form a final braided product, preferably a surgical suture. The preferred apparatus includes means for controlling tension on the yarns dispensed from the bobbins to form the braided suture product and to control the tension on the final braided product. Each yarn carrier includes a spindle onto which a novel molded bobbin having a central aperture is mounted for rotational movement relative to the spindle. Each bobbin has a number of radial segments engageable with a pawl on the carrier for selectively permitting rotation of the bobbin in response to yarn tension in order to control the dispensing of yarn from the bobbin.

In accordance with the invention, a bobbin top holder base is fixedly mounted relative to the yarn carrier adjacent the top of the yarn carrier spindle and, hence, adjacent to the top of a bobbin situated thereon. The bobbin top holder base has hinge pins, and a bobbin top holder is hingedly mounted to the bobbin holder base at the hinge pins. The bobbin top holder has two longitudinally extending legs defining a slot therebetween and, more specifically, a spindle engaging recess having an inwardly projecting radiused section to engage a corresponding circumferential recess in the spindle adjacent the spindle tip. The bobbin holder legs are formed of a resilient plastic material which is sufficiently flexible to permit the legs to spread apart as the legs are forced over the spindle tip, and resiliently reassume a rest position disposed within the circumferential recess of the spindle to hold the bobbin on the spindle.

In use, the bobbin top holder first is disposed in an unlocked or open position rotated away from the spindle to permit mounting of a bobbin loaded with yarn onto the carrier. After the bobbin is mounted, the bobbin top holder is rotated into contact with the spindle tip with sufficient force to cause the bobbin top holder legs to spread apart and mount over the spindle, resiliently resuming a rest or contracted position disposed within the circumferential recess of the spindle tip, thereby securing the bobbin on the carrier. The braider apparatus thereafter is operated to form a final braided product, preferably a surgical suture. In order to remove an empty bobbin, sufficient upward force is exerted on the bobbin holder legs to cause the bobbin legs to spread apart, leave the spindle recess, and become disengaged from the spindle. The preferred bobbin holder is injection molded of an elastomeric plastic material which is sufficiently resilient to permit many cycles of bobbin mounting without failure of the bobbin top holder.

The bobbin holder of the invention is convenient to use and advantageously improves the efficiency of the preferred braider apparatus.

BRIEF DESCRIPTION OF THE DRAWINGS

Preferred embodiments of the invention will be described herein with reference to the drawings, wherein:

FIG. 3 is an elevational view, partially in cross-section, of the preferred yarn tension control system of the invention;

FIG. 4 is a partial cross-sectional view taken along lines 4—4 of FIG. 1 illustrating a yarn carrier engaged with a carrier plate and the main support plate;

DETAILED DESCRIPTION OF THE PREFERRED EMBODIMENTS

Figure 1:
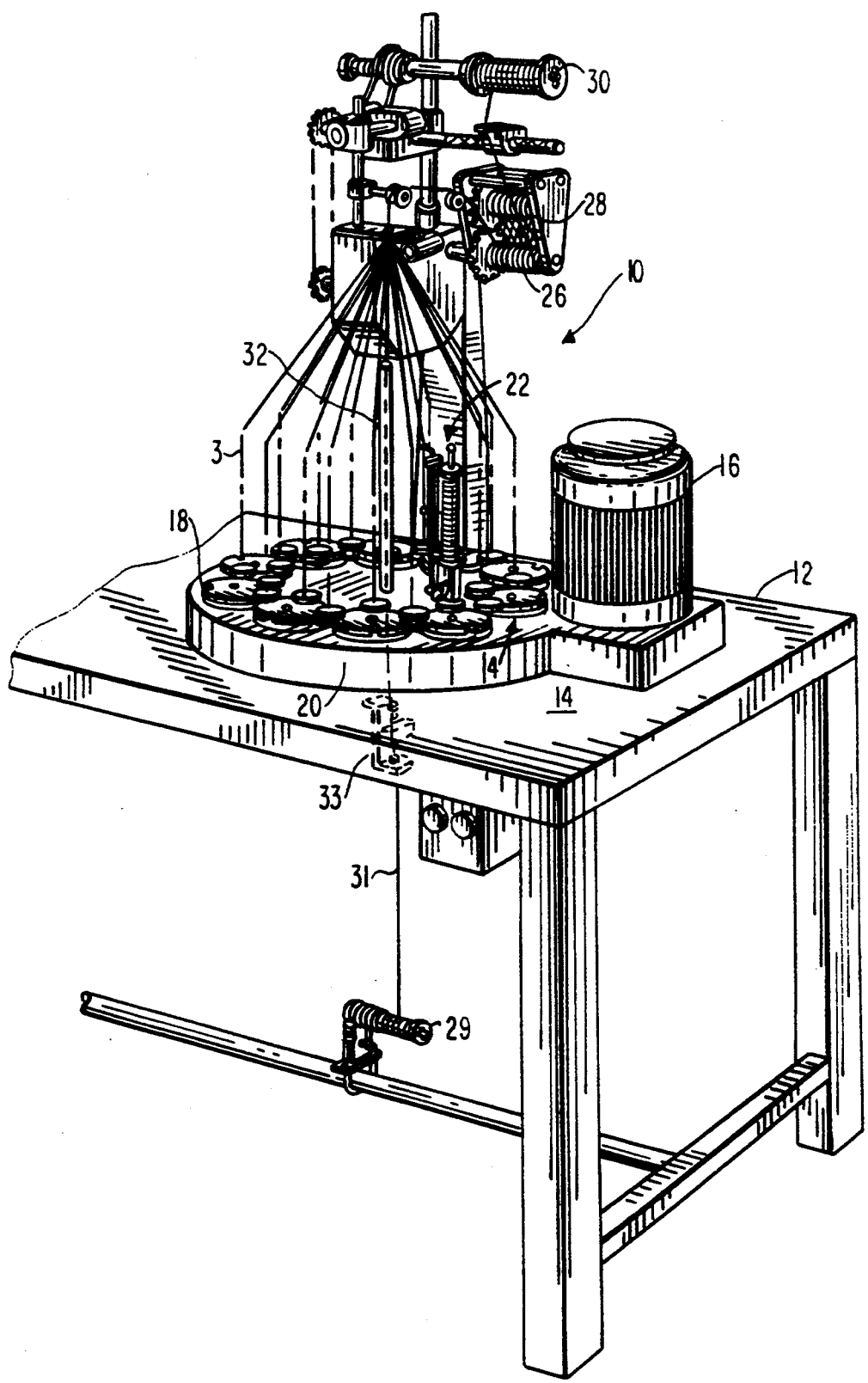
FIG. 1 is a partial perspective view of a braider apparatus for braiding fine denier yarns constructed in accordance with the preferred embodiment of the invention.

Referring initially to FIG. 1, there is illustrated an apparatus 10 for braiding sutures constructed according to the present invention. The apparatus 10 is supported on frame 12 which includes a horizontal support plate 14. Electrically powered motor 16 is arranged to drive the apparatus as will be described. In operation, motor 16 drives carrier plates 18 around main carrier support plate 20 along a predetermined path. A plurality of yarn bobbin carriers 22, only one of which is illustrated in FIG. 1 for simplicity, are mounted to carrier plates 18 and dispense yarns from yarn bobbins 24 (see FIG. 6) as the bobbins and carriers follow a predetermined path around the main carrier support plate. The apparatus illustrated in FIG. 1 is designed to drive the bobbin carriers in undulating paths in opposite directions around the main carrier plate in a known manner. However, alternate carrier path configurations also are contemplated, such as a spiral pattern in which all bobbin carriers move in the same direction around the main carrier plate. Spiral braiders, per se, are also known.

As illustrated in FIG. 1, yarns 3 dispensed from each bobbin carrier station are led to a braiding zone and formed into an elongated braided suture product. Tension on the braided suture product is controlled by driven tension rollers 26, 28 and take-up roller 30. Optionally, a core yarn bobbin 29 is mounted beneath support plate 14. The optional core yarn 31 maintained under tension is led through a core yarn tension detector 33 and a hollow tube 32 to the braiding zone, such that sheath yarns from the yarn carriers mounted on main carrier plate 20 are braided about the core yarn.

Referring now to FIGS. 2-4 and 6 the yarn carrier system and yarn tensioning system is illustrated. Referring initially to FIG. 4, there is shown a cross-sectional view of the base of a yarn carrier 22 mounted to carrier support plate 18. Carrier 22 has downwardly extending connector shoes 38, 40 which extend into guide channels in the main carrier support plate 20. The connector shoes traverse the respective guide channels as the yarn carrier is transferred between the respective carrier support plates 18. In an alternative contemplated arrangement the carriers are transported around the main carrier support plate in a spiral pattern.

Figure 2:
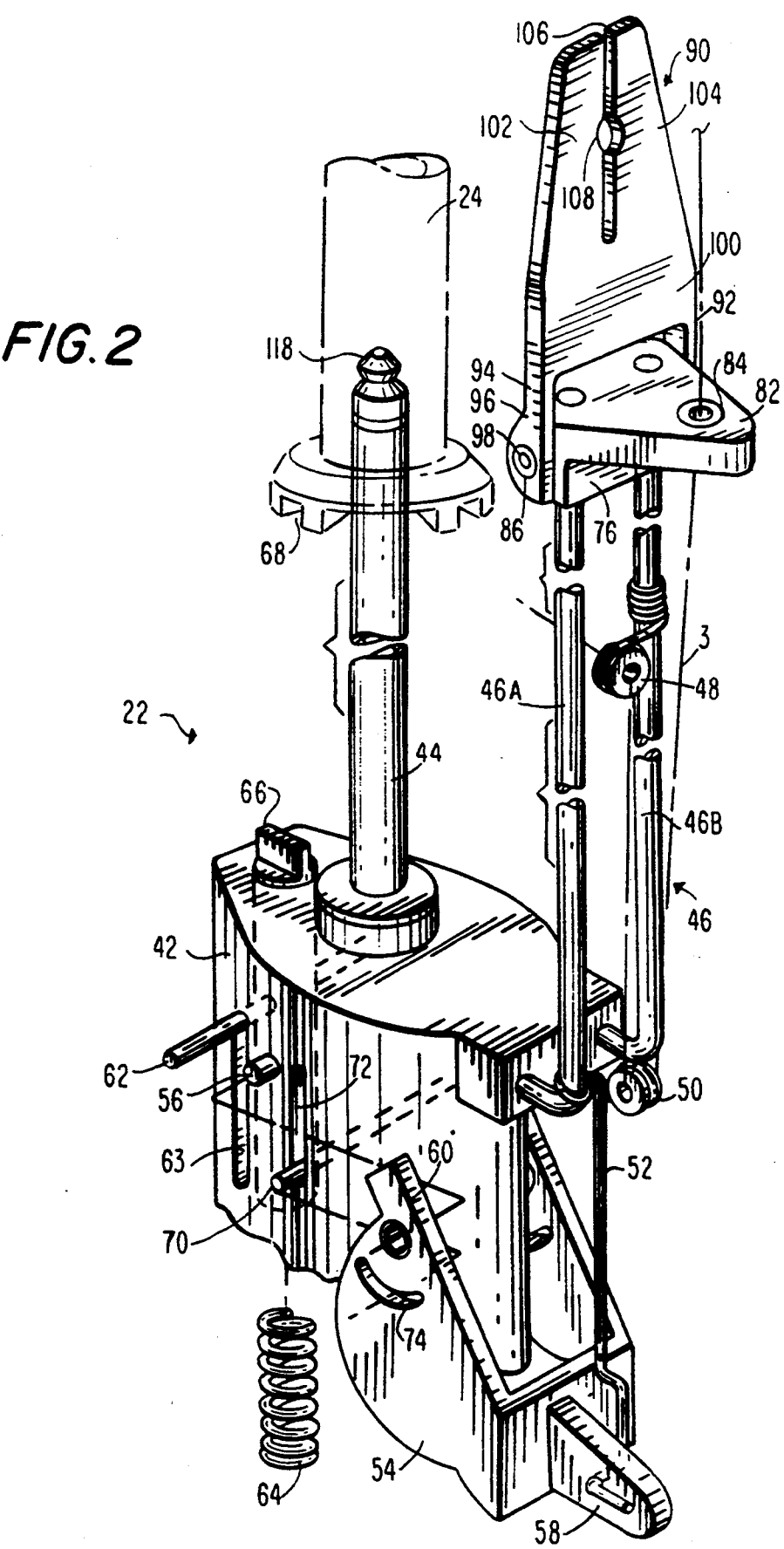
FIG. 2 is a partial perspective view with parts separated for convenience of illustration, showing the carrier housing assembly and bobbin top holder contructed in accordance with the preferred embodiment of the invention.
Figure 11:
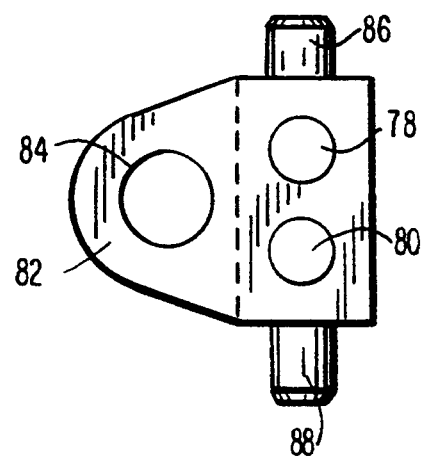
FIG. 11 is a top plan view of the bobbin top holder mounting base of FIG. 10.

As shown in FIGS. 2-3, yarn bobbin carrier 22 has a carrier housing 42 with a spindle 44 extending vertically therefrom to receivably engage bobbin 24. A yarn guide support 46 also extends from carrier housing 42 in a direction substantially parallel to spindle 44, and is shown in FIG. 2 as a pair of rods 46A and 46B. A yarn dispensing guide eyelet 48, preferably made from a ceramic material, is fixed to one A compensator eyelet 50, also preferably made from a ceramic material, slidably engages the other rod. Compensator eyelet 50 is connected via a compensator rod 52 to a compensator arm 54 for controlling the dispensing of yarn in response to tension exerted by the yarn on compensator arm 54 via compensator rod 52 and eyelet 50. Compensator arm 54 pivots about pivot pin 56 on carrier 22, as shown in FIG. 3. End portion 58 of compensator arm 54 is connected to compensator rod 52 while the opposite end portion 60 of pivot arm 54 engages pin 62 which is biased upwardly a light coil spring 64. Pin 62 is disposed in and moves upwardly and downwardly in slot 63. Pin 62 is connected to pawl 66 and arranged to float into and out of radial slots 68 on the lower surface of yarn bobbin 24. Pin 70 moves upwardly and downwardly in slot 72 in carrier housing 42 while traversing the moving arcuate slot 74 in compensator arm 54. Pin 62 is biased upwardly by spring 64 and, in turn, biases end portion 60 upward, pivotally rotating compensator arm 54 to urge arm end 58, rod 52 and compensator eyelet 50 downwardly. The upper ends of rods 46A and 46B are seated in and support a top holder support 76. Top holder support 76 has two substantially parallel vertical apertures 78, 80 configured to receive rods 46A, 46B, as by frictional engagement or by an adhesive disposed therebetween (see FIG. 11). Top holder support 76 includes a substantially horizontal yarn guide section 82 extending from support 76 and having a ceramic yarn guide eyelet 84 for guiding yarn dispensed from the bobbin toward the braiding zone. Top holder support 76 also has a pair of hinge pins 86, 88 (see FIG. 11) extending longitudinally therefrom in a direction substantially perpendicular to the spindle. Bobbin top holder 90 has a pair of hinge pin engaging legs 92, 94. Each leg has an enlarged hinge pin receiving section 96 having a hinge pin aperture 98 configured and dimensioned to receive hinge pins 86, 88. In this manner bobbin top holder 90 is mounted to top holder support 76 and is hingedly rotatable about the axis of hinge pins 86, 88.

Figure 7:
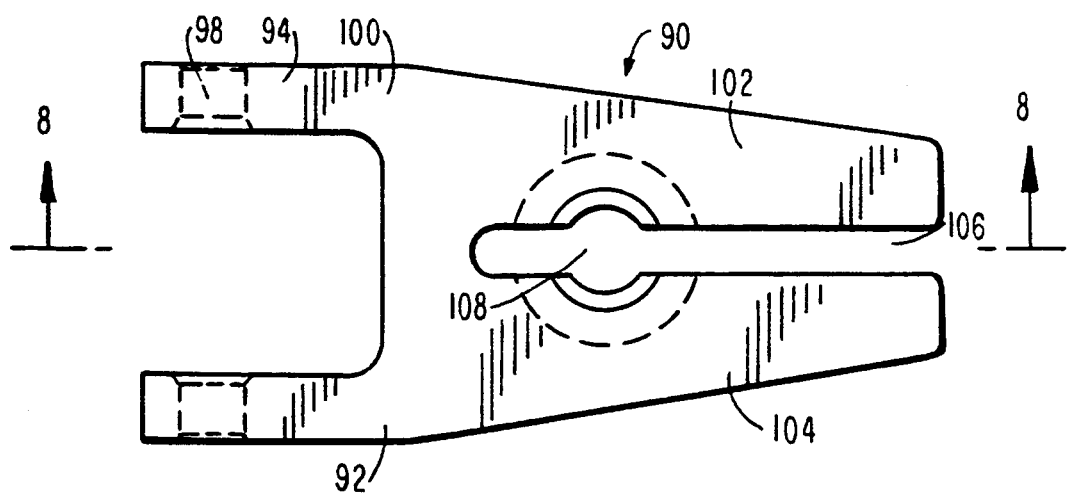
FIG. 7 is a top view of the bobbin top holder constructed in accordance with the preferred embodiment of the invention.
Figure 8:
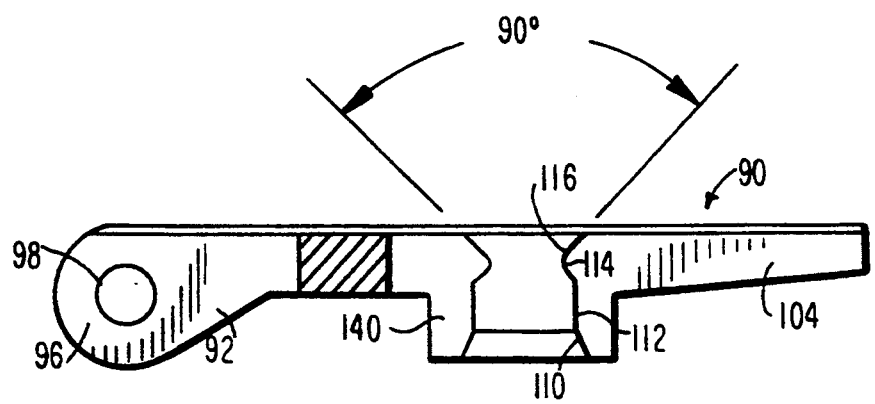
FIG. 8 is a cross-sectional view of the bobbin top holder taken along lines 8—8 of FIG. 7.

Bobbin top holder 90 has a substantially planar section 100 extending from legs 92, 94 and a pair of spindle gripping legs 102, 104 defining therebetween a slot 106 and a spindle engaging recess 108. FIG. 7 is a top plan view of bobbin holder 90. Referring now to FIG. 8, a cross-sectional view of the bobbin holder taken along lines 8—8 of FIG. 7, it can be seen that spindle engaging recess 108 is configured with an outwardly tapered entrance wall 110, a substantially cylindrical barrel section 112, an inwardly projecting radiused section 114, and an outwardly tapered exit wall section 116. Preferably, entrance wall defines an angle of about 10° to 20° relative to the axis of recess 108, and exit walls 116 define an included angle on the order of about 90°. The spindle engaging recess is symmetrical about its vertical axis, except for slot region 106, and is identically configured in both legs 102, 104. As shown in FIG. 8, spindle engaging recess 108 is disposed in a region 140 of legs 102, 104 of greater thickness than the remaining portions of the legs in order to provide structural support surrounding the spindle engaging recess.

Figure 6:
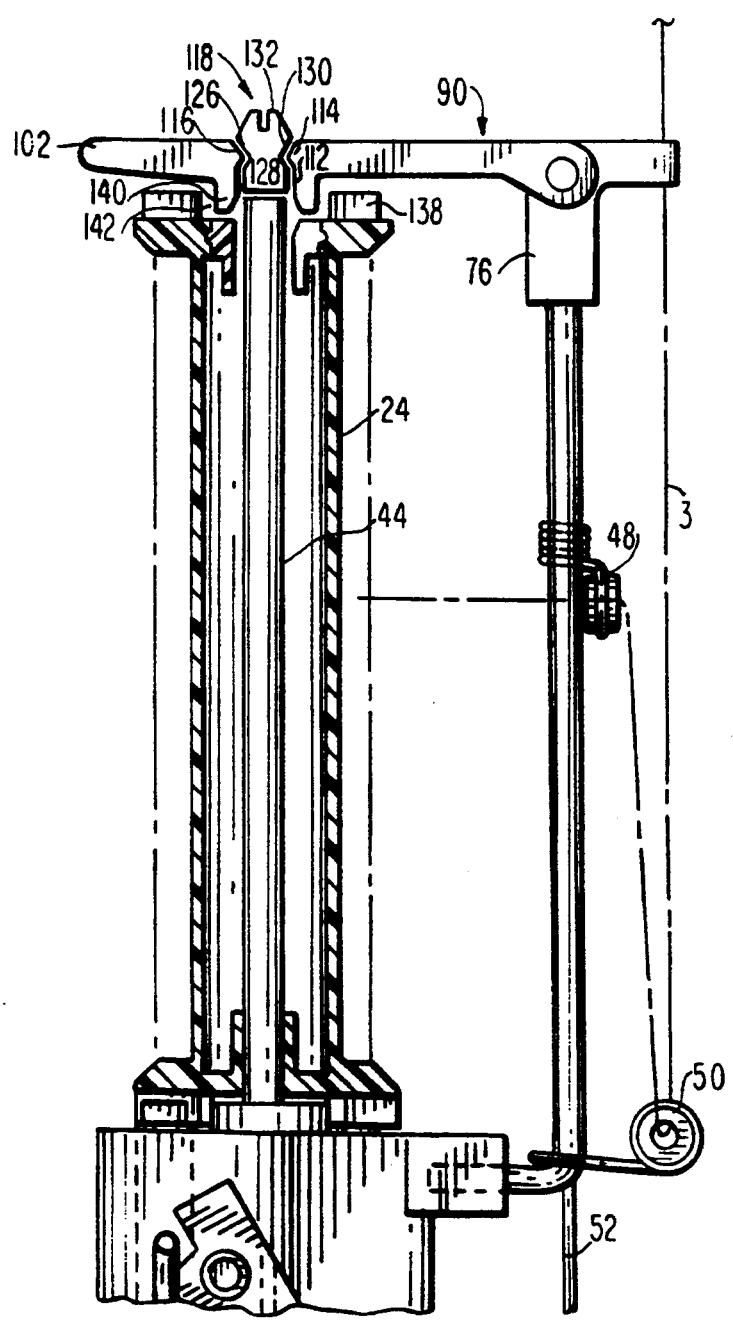
FIG. 6 is an elevation view of the bobbin, carrier, and bobbin top holder assembly constructed in accordance with the preferred embodiment of the invention, illustrating the bobbin in cross-section.
Figure 9:
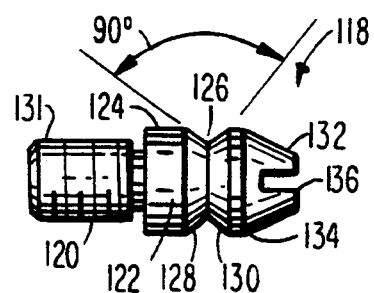
FIG. 9 is an elevation view of the spindle tip constructed in accordance with the preferred embodiment of the invention.
Figure 10:
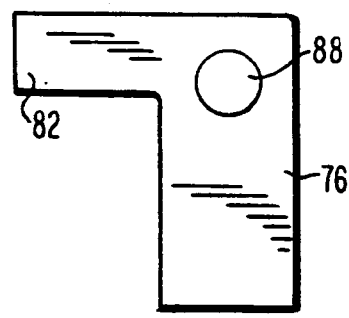
FIG. 10 is an elevational view of the bobbin top holder mounting base constructed in accordance with the preferred embodiment of the invention.

Referring again to FIG. 2, spindle 44 is provided with a bobbin holder engaging tip 118 configured to be disposed in spindle engaging recess 108 to secure bobbin top holder 90 to spindle 44 and, hence, bobbin 24 on spindle 44 (see FIG. 6). The preferred spindle tip configuration for engaging recess 108 is illustrated in FIG. 9. As shown in FIG. 9, spindle tip 118 has a spindle engaging shank 120 connected to a spindle tip body 122. Spindle tip body 122 has a substantially cylindrical proximal base 124, a spindle tip recess 126 defined by a pair of inclined walls 128, 130, and a substantially frusto-conical distal tip section 132. Distal tip section 132 and recess 126 may be joined by a substantially cylindrical transition section 134. Shank 120 is configured to be received in a hollow recess in spindle 44 to fixedly mount spindle tip 118 to spindle 44. Fixed mounting of tip 118 to spindle 44 may be accomplished by friction fit of shank 120 in the spindle recess, by providing an adhesive or combination of adhesive and friction between the shank and recess, or most preferably by providing mutually engageable threads on the shank and within the recess. In the preferred embodiment wherein threads 131 are provided, a slot 136 may be provided in distal tip 132 for engaging a tool, such as a screwdriver. Inclined walls 128, 130 preferably define an interior angle on the order of about 90°, and the walls of frusto-conical distal tip 132 preferably define an angle of about 20° relative to the tip axis. As in the case of spindle engaging recess 108, spindle tip 118 preferably is symmetrical about the axis thereof.

Figure 5:
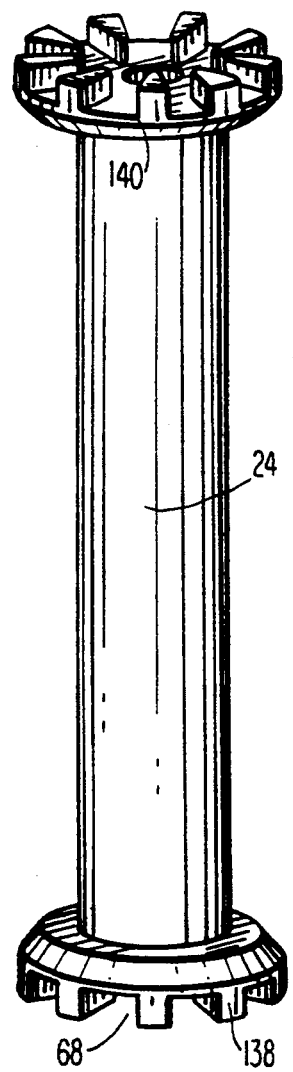
FIG. 5 is a perspective view of the preferred bobbin.

Referring now to FIG. 5, the bobbin 24 preferred for use with the unique yarn dispensing system according to the present invention is shown. Bobbin 24 is integrally constructed of a lightweight material such as molded nylon or other plastic material. The bobbin is constructed to have an overall weight of about 20 grams and a minimum diameter dimensioned so as to reduce inertial forces on the delicate yarns used to make the braided suture. In order to reduce tension on the yarns further, the number of radial segments 138 which control the release point of the bobbin have been reduced to nine segments as shown. The bobbin includes a hollow cylindrical opening 140 configured to slidably receive spindle 44 with bobbin 24 being rotatable about the spindle (see FIGS. 2 and 6).

In contrast, in prior art bobbin and carrier assemblies a metal bobbin is mounted over a shaft and engages and is fixed by screw mounting so as not to rotate relative to the top surface of a metal plate on the carrier. The bottom surface of the metal plate has twelve or more segments to engage the carrier pawl. The prior art bobbins are also of smaller diameter than the bobbins of the present invention, and yet weighed about 50 grams. The combined bobbin and and metal plate adaptor of prior art braiders have a total weight of about 85 grams. The increased diameter and light weight of the present bobbin, together with the integral pawl engaging segments and reduced number thereof, further reduce the force which must be exerted on the yarn in order to unwind the yarn from the bobbin.

In particular, the unique braider bobbin of the present invention is specifically constructed to adapt the apparatus for braiding fine denier yarns applicable to fine sutures and is preferably constructed having the following characteristics:

a) reduced mass integrally molded nylon construction of approximately 20 grams, as compared to prior art bobbins of approximately 50 grams, and prior art bobbin and adaptor assembly weighing about 85 grams;

b) reduced number of pawl engaging segments 138 which are integrally molded with the bobbin, preferably 9 segments, not more than 11, versus prior separate adaptor structures having 12 or more pawl engaging segments and higher mass. This structure produces greater circumferential spacing between segments, permitting improved engagement by pawl 66 at high rotational speeds;

c) bobbin diameter approximately 20 mm as compared to lesser diameter prior art bobbins. This feature reduces the tension force on the yarn required to turn the bobbin and stabilizes the bobbin and yarn movements; and d) unitary construction bobbin, injection molded nylon 6 or other moldable plastic permitting relatively large diameter bobbin at reduced weight with close tolerances (i.e. ±0.15 mm) for precision in winding from flange to flange.

In use, bobbin 24 is mounted onto spindle 44 with the bobbin top holder 90 in the open or unlocked position, as shown in FIG. 2. When mounted, radial slots 68 on bobbin 24 engage pawl 66 on carrier housing 42. Braiding yarn 3 is led from bobbin 24 through dispensing eyelet 48, compensator eyelet 50 and guide eyelet 84 and upward to the braiding zone (also see FIG. 6). As will be explained in greater detail below, bobbin top holder 90 is rotated and locked into the position shown in FIG. 6 to hold bobbin 24 on spindle 44 during braiding.

During operation of the braiding apparatus, yarn is drawn upwardly by the braiding system. Yarn is dispensed from bobbin 24 until the tension on the yarn exceeds a predetermined value and draws compensator eyelet 50, rod 52 and compensator arm end portion 58 upward (see FIGS. 2-3). The opposite end 60 of arm 54 depresses pin 62 against spring 64, causing pawl 66 to withdraw from slot 68 in the bobbin 24. Removal of pawl 66 from slot 68 permits bobbin 24 to rotate about spindle 44 to dispense more yarn. As further yarn is dispensed, the tension in the yarn is reduced below a predetermined value until the force of spring 64 again urges arm end portion 60 upward, rotatably pivoting arm 54 so that end portion 58, rod 52 and compensator eyelet 50 move downward. Pawl 66 simultaneously re-enters radial slot 68 in bobbin 24 to prevent further rotation of the bobbin until the cycle is repeated.

Preferably, fine denier multifilament yarns in the range of about 0.2 to 6.0 denier are dispensed from bobbin 24, with the tension of the yarn dispensed from bobbin 24 closely controlled within a precise range. The tension of the yarns is controlled within a precise range, particularly by selecting a spring 64 which is within a predetermined range of spring rates. Prior art braiders utilized a spring 64 of significantly greater spring rate than is contemplated herein due to the fact that braiding was accomplished with heavier braiding materials. In addition, in prior art braiders pin 70 was also arranged to be biased downwardly by a spring positioned centrally within spindle shaft 44. In the present apparatus the central spring has been eliminated and spring 64 has been selected to have a reduced spring rate in the range of from about 0.6 to 0.7 pounds per inch. The standard spring on such braiders having a much higher spring rate on the order of about 0.9 to about 1.0 pounds per inch. Reducing the spring rate reduces the tension force on the yarn necessary to cause pivot arm 54 to rotate and withdraw pawl 66 from slot 68, thereby permitting the bobbin to rotate and pay out additional yarn. The reduced spring rate accommodates the relatively lower tensile strength associated with yarns of aforementioned preferred denier range suitable for producing braided sutures. The production of such sutures is thus carefully and precisely controlled to accommodate the fine character, not only of the finished braided suture, but particularly of the yarn components thereof.

As previously noted, bobbin 24 is constructed of a lightweight moldable material such as nylon and defines a central axial opening 140 extending the length of the bobbin to receive the carrier housing spindle (see FIGS. 2 and 6). With bobbin holder 90 disengaged from spindle 44 and rotated away from the spindle, such as in the substantially vertical bobbin holder position shown in FIG. 2, the bobbin may be mounted over the spindle with spindle 44 received within opening 140. Referring now to FIGS. 2 and 6-9, after bobbin 24 is mounted over spindle 44 with pawl 66 seated in a bobbin slot 68, bobbin holder 90 is rotated about hinge pins 86, 88 until inwardly projecting radiused section 114 on each bobbin holder leg 102, 104 contact the angled surface of frusto-conical distal tip section 132. Preferably, contact between section 114 and tip section 132 occurs slightly before holder 90 reaches a position perpendicular to the axis of spindle 44. Exerting force on holder 90 to urge holder 90 against spindle tip 118 causes holder legs 102, 104 to be spread apart slightly by the camming action of frusto-conical tip 132 against section 114. Legs 102, 104 are spread apart until radiused section 114 is mounted over the distal tip section 132 and thereafter resiliently return to their rest position and become disposed within recess 126, as shown an FIG. 6. Thus, maximum spreading of legs 102, 104 occurs when radiused section 114 is disposed at cylindrical section 134 having substantially the same diameter as spindle tip base 124. In the locked or hold down position illustrated in FIG. 6, inwardly extending radiused section 114 is disposed in recess 126 with outwardly extending exit wall 116 juxtaposed to distal recess wall 130 and the lower radiused section 114 disposed adjacent proximal inclined recess wall 128. Cylindrical section 112 is disposed around spindle tip base 124. As shown in FIG. 6, the maximum diameter of tip 118 approximates the diameter of spindle 44 to facilitate mounting and removal of the bobbin onto and from the spindle.

Referring again to FIG. 6, with bobbin top holder 90 in the locked or hold down position engaging spindle tip 118 the relatively thick section 140 is disposed within the open area 142 on bobbin 24 radially within radial segments 138, with the remaining portions of legs 102, 104 disposed above and away from radial segments 138. In the event bobbin 24 rides up slightly, as may occur during yarn dispensing, thick section 140 abuts the flat central region on the end of the bobbin to prevent further upward movement of the bobbin. However, at no time does bobbin holder 90 engage radial segments 138 or otherwise obstruct rotational movement of the bobbin about spindle 44.

In order to remove a bobbin from the apparatus, i.e. after all the desired yarn has been dispensed from the bobbin during braiding, upward force is exerted on bobbin top holder 90, such as at the distal areas of legs 102, 104. This causes inclined wall 130 on tip 118 to cam against exit wall 116 of recess 126 and spread apart legs 102, 104, thereby causing inwardly projecting radiused section 114 to spread apart and become disengaged from recess 126. As radiused section 114 is removed from spindle 118 over frusto-conical distal tip 132, bobbin top holder legs 102, 104 resiliently return to their rest position wherein the separation distance of radiused sections 114 on each leg approximates the minimum diameter of spindle tip 118 within recess 126. At this point bobbin top holder 90 may be further rotated about hinge pins 86, 88 until holder 90 is rotated to a position such as shown in FIG. 2 out of the way to permit removal of the empty bobbin and/or placement of a new bobbin loaded with yarn to be dispensed for braiding.

The bobbin carrier and spindle may be made of metal, such as stainless steel, with top holder support rods 46A, 46B made from the same or different metal, e.g. aluminum, or a rigid plastic material. Ceramic eyelet 48 may be mounted to rod 46B by wrapping a metal wire around both the eyelet and the rod to fix the eyelet to a central region of the rod. Ceramic eyelet 50 may be mounted to rod 46A by similarly wrapping a metal wire around the eyelet and around rod 46A, to permit slidable movement of the wire relative to rod 46A. Preferably, compensator rod 52 is integrally formed of the same wire which connects ceramic eyelet 50 to rod 46A. This may be accomplished by wrapping the wire around eyelet 50, looping the wire around rod 46A, and extending the wire to engage compensator arm end section 58, as illustrated in FIGS. 2–3. Top holder support 76 preferably is made of a rigid plastic material, such as nylon. Top holder 90 is made of a plastic material which is sufficiently flexible and resilient to deform and permit legs 102, 104 to repeatedly be spread apart and mounted over spindle tip 118 through multiple cycles, such as an elastomeric nylon material. Advantageously, both top holder support 76 and bobbin top holder 90 may be injection molded at relatively modest cost. Spindle tip 118 should be made of a rigid metal material, such as a zinc coated steel.

As will be appreciated, the bobbin top holder of the present invention facilitates quick and easy placement and removal of a bobbin relative to the spindle and bobbin carrier. Advantageously, the top holder of the invention does not require any pinching or gripping action by the user, such as to unscrew a prior bobbin holder, thereby minimizing the effort which must be exerted by the user to engage or release the bobbin top holder and reducing the time required to change bobbins on the carrier. These reductions in exerted energy and time contribute to increased efficiency in the braiding operation, which efficiencies become considerable in operating a large number of braiding apparatus each having multiple yarn carriers.

Figure 12:
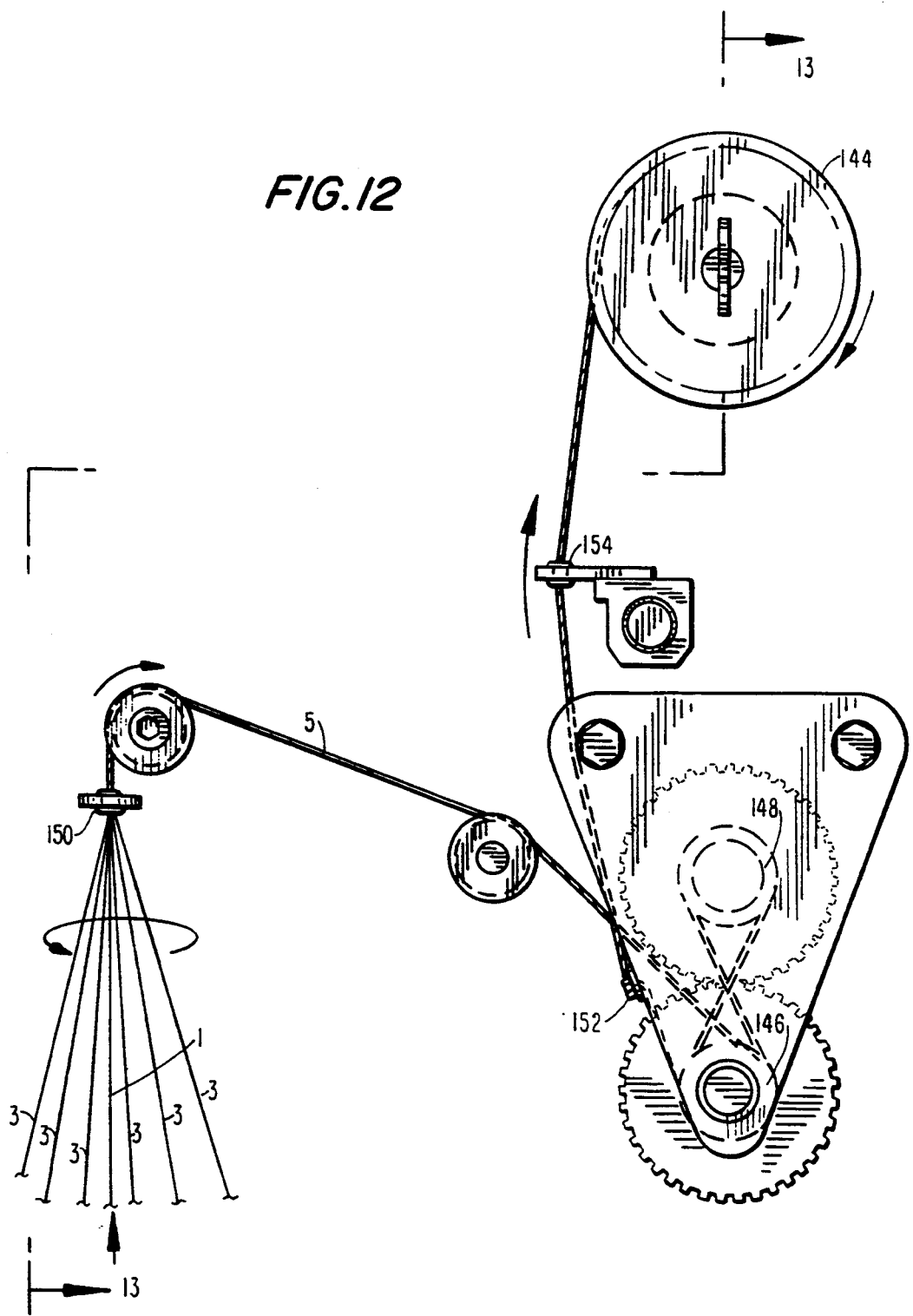
FIG. 12 is a partial schematic view illustrating the path of the yarns and the formation of a braided suture on the present apparatus.

Referring now to FIGS. 12–15, the take-up system for the braided suture product is illustrated. FIG. 12 illustrates the final formation of the braided suture and the take-up roller system leading to final winding of the finished product on take-up spool 144. In particular, core yarn 1 and sheath yarns 3 are formed into a final braided suture 5 which is first directed to take-up "tensioning" rollers 146, 148 and thereafter to final take-up spool 144 where the product is systematically wound in uniform layers about the spool. The braided product 5 is wound continuously about rollers 146, 148 to stabilize the product prior to winding about take-up spool 144. Ceramic eyelets 150, 152 and 154 guide the suture from the braiding zone to the take-up rollers and then to the take-up spool without abrasion or other damage.

Figure 13:
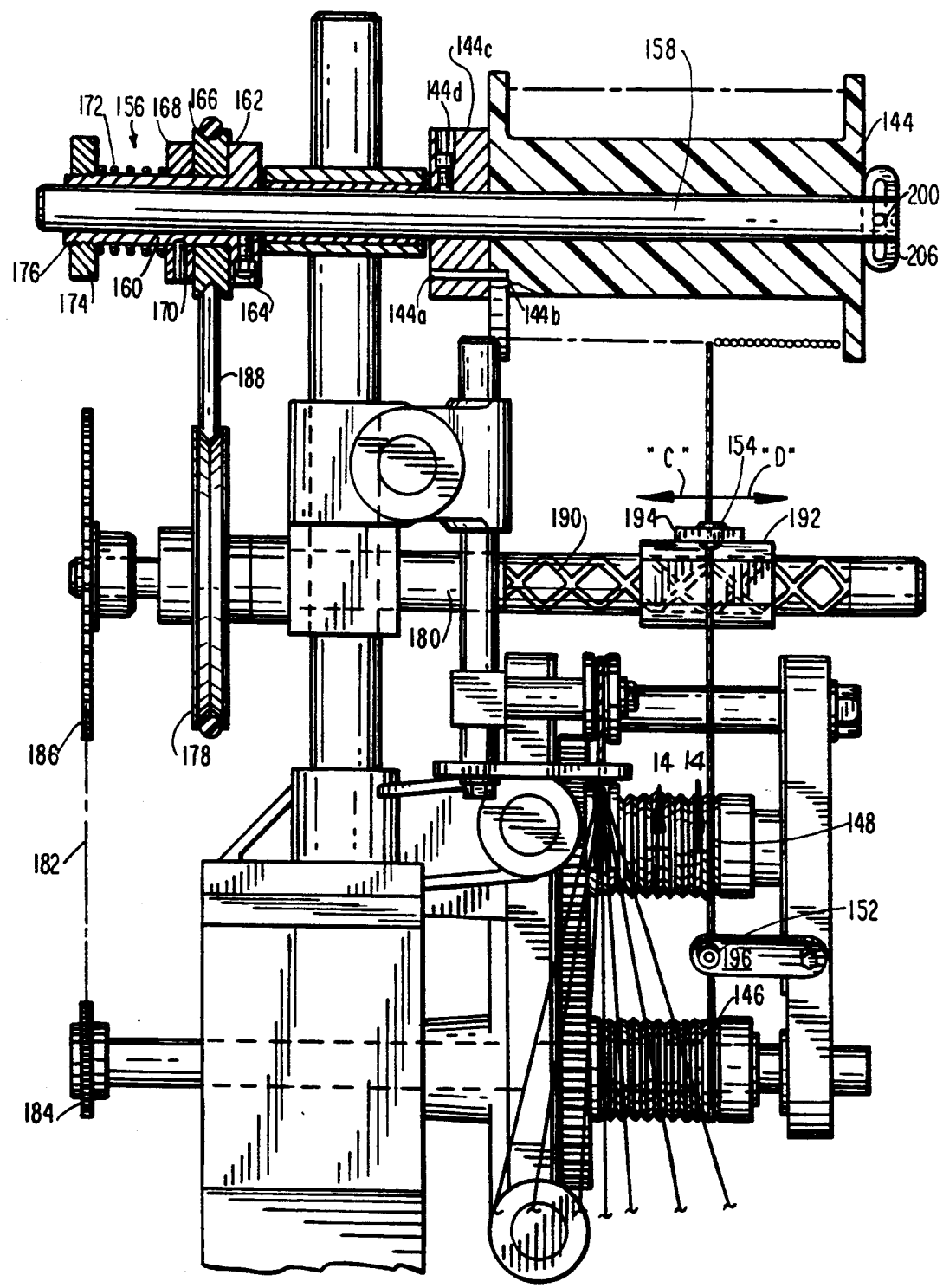
FIG. 13 is a cross-sectional view taken along lines 13—13 of FIG. 12 illustrating the take-up rollers and take-up clutch which form part of the invention.

Take-up clutch 156 is shown in FIG. 13 to precisely control the tension on the finished product via final spool 144. Clutch 156 is mounted on spool shaft 158 and includes internal clutch shaft 160 having first clutch plate 162 at one end secured to shaft 158 by set screw 164 for rotation with the shaft. Molded nylon pulley wheel 166 is slidably positioned over clutch shaft 160 for slidable rotation relative to clutch plate 162. Second clutch plate 168 is connected by screw 170 for rotation with clutch shaft 160. Screw 170 is fitted loosely in a slot (not shown) for movement in the longitudinal direction of shaft 160 to permit clutch plate 168 to move toward and away from pulley wheel 166 by pressure of coil spring 172 when spring 172 is compressed by turning knurled wheel 174 which is fitted by threads 176 about the end of shaft 160 as shown. Thus, by threadedly rotating wheel 174 clockwise to advance the wheel toward the spring 172 the force transmitted by the spring on the clutch plate 168 is increased, thereby increasing the friction forces between pulley wheel 166 and clutch plates 168 and 162. By turning wheel 174 counterclockwise, the wheel moves outwardly of shaft 160 and the spring force is reduced thereby reducing the friction forces and permitting free rotation of pulley wheel 166.

Referring further to FIG. 13, pulley wheel 178 is connected to shaft 180 which is driven by chain 182 shown schematically in the FIG. Chain 182 is powered by power driven sprocket 184 and thereby produces rotation of shaft 180 via large sprocket 186 at a reduced rate of rotation in accordance with the selected ratio of the size of sprocket 184 to the size of sprocket 186. Pulley wheel 178 is in turn connected to endless drive belt 188 which is fabricated of a suitable, flexible elastomer material and has a circular cross-section and elongated construction.

Referring once again to FIG. 13, shaft 180 contains diamond shaped guide grooves 190 for reception of similarly shaped members formed integrally with product guide member 192 such that continuous rotation of shaft 190 will produce alternating repeating movement of the guide member 192 arranged to move in the direction of arrows "C" and "D" as the shaft 190 rotates. Plate 194 attached to guide member 192 contains ceramic suture guide 154 which guides the finished braided suture received from take-up rollers 146, 148 through ceramic guide 152 affixed to support arm 196 to take-up spool 144.

In operation, as shaft 180 rotates, guide member 192 traverses the right hand portion of the shaft. The guide member 192 alternates from the direction of arrow C to the direction of arrow D in a repeating manner to guide finished braided suture product onto spool 144 in successive uniform and even layers. The tension on the braided suture may be selectively increased or decreased as desired, by turning clutch adjustment knob 174 as described previously. The capability to adjust the tension on the finished product as it is being wound onto spool 144 is significant. As the diameter of the final package increases, the ratio of the linear speeds between the take-up spool 144 and the grooved rollers 146, 148 increases thereby increasing the tension on the finished product. Adjustment of the tension on the finished product is then possible by adjusting clutch 156 to maintain appropriate tension on the suture with a high degree of accuracy and control.

Figure 14:
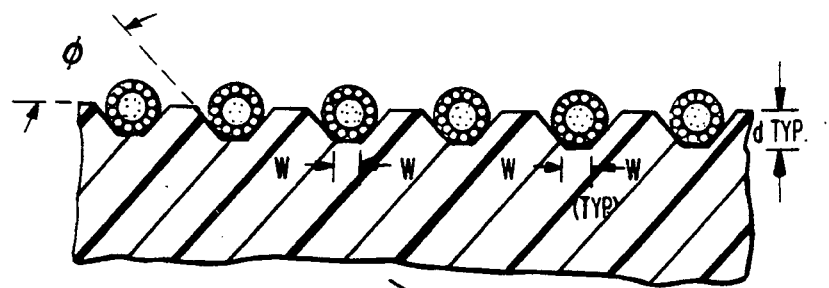
FIG. 14 is a cross-sectional view taken along lines 14—14 of FIG. 13 illustrating the novel take-up spool constructed according to the invention.

Referring once again to FIG. 13 in conjunction with FIG. 14, the braid take-up roller system is illustrated. As can be seen in FIG. 14, the take-up rollers 146, 148 are configured to include relatively sharp "V-shaped" grooves for braided suture take-up to facilitate appropriate contact with braided suture products of a wide range of sizes, including extremely small suture diameters. Further, since the braid is continuously wrapped around the rollers 146, 148, it has been found that it is possible to increase the number of grooves, i.e. wraps, for a given length of rollers, thereby increasing the friction contact area between the braided suture product and the rollers. This facilitates increased control over the finished braided suture product and minimizes slippage between the suture and the rollers. Preferably, the suture is wound around take-up rollers 146, 148 in a FIG. 8 configuration, as shown in phantom in FIG. 12.

Figure 17:
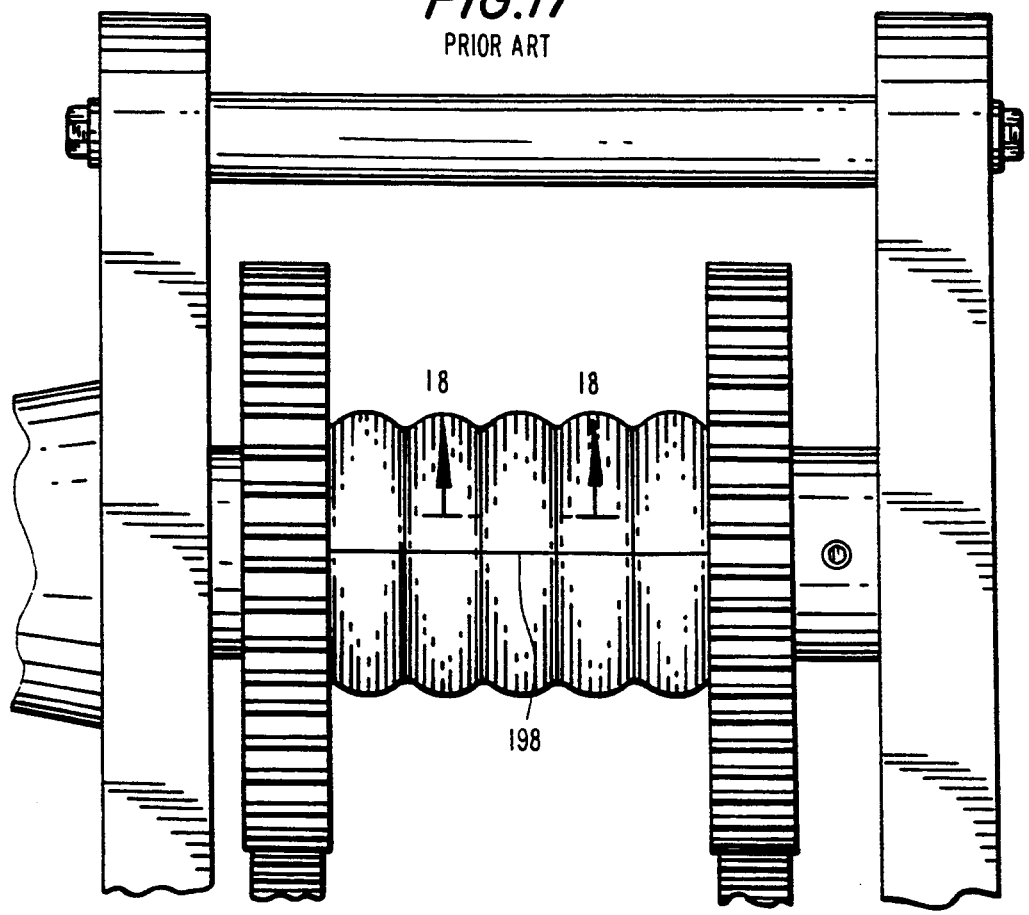
FIG. 17 is an elevational view of a take-up spool contructed according to the prior art.
Figure 18:
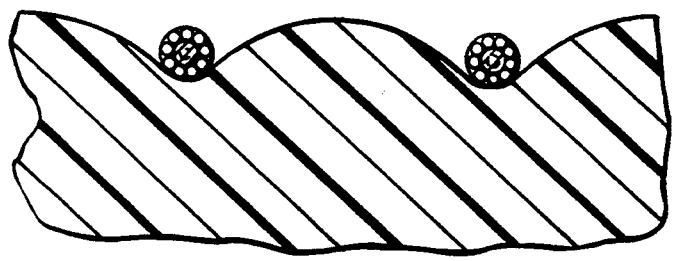
FIG. 18 is a greatly enlarged cross-sectional view taken along lines 18—18 of FIG. 17, illustrating the surface of the prior art take-up spool of FIG. 17.

As can be seen in comparing the rollers shown in FIGS. 13 and 14 with the prior art rollers (see FIGS. 17 and 18), it will be readily appreciated that the contact between the product and the rollers is increased with the rollers constructed according to the present invention as shown in FIGS. 13 and 14. In addition, it is noted that the take-up rollers constructed according to the invention are of machined plastic material, such as nylon, as opposed to the molded prior art rollers shown in FIGS. 17 and 18. The prior art rollers were of molded construction and included mold part lines 198, an imperfection which does not adversely affect braided products of heavy duty construction, i.e. rope construction; however, the braiding of fine denier sutures as contemplated herein requires take-up rollers of improved construction having smooth surfaces which not only avoid adverse affects on the suture product, but which also produce sufficiently controlled friction to permit take-up of the product without damage. The smooth surfaces of the machined plastic rollers 146, 148 as shown in FIGS. 13 and 14 achieve these objectives.

Referring to FIG. 14, the take-up rollers of the present invention are machined to include grooves having inclined side walls terminating in a flat bottom surface. The overall depth "d" of the groove should be dimensioned to accommodate a range of suture sizes. A depth range of about 0.1 to 0.2 inches may be appropriate, and a depth of about 0.16 inches is preferred. The width of the flat bottom of the groove, shown as dimension "w" in FIG. 14, is preferably about 0.002 inch. The inclined surfaces define an angle $\phi$ with the outer surface of the take-up roller. It has been found that appropriate angles are within the range 55° to 65°, and preferably about 60°.

Figure 15:
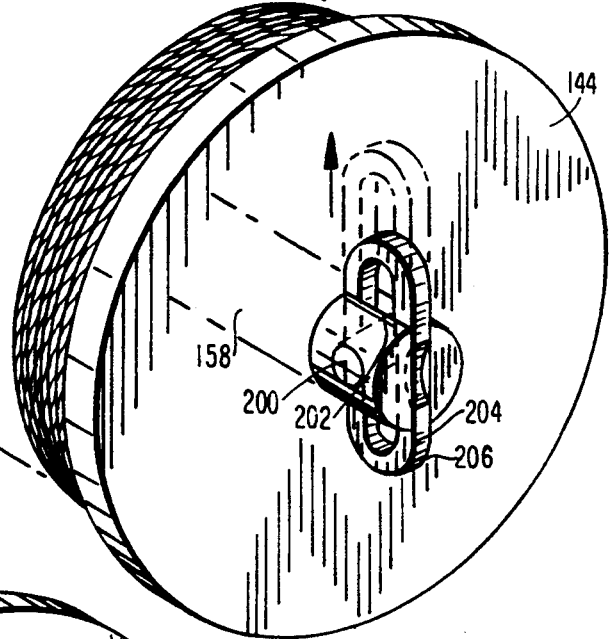
FIG. 15 is a perspective view of the quick-release system in the locked position for retaining the take-up spool on the apparatus of the invention.
Figure 16:
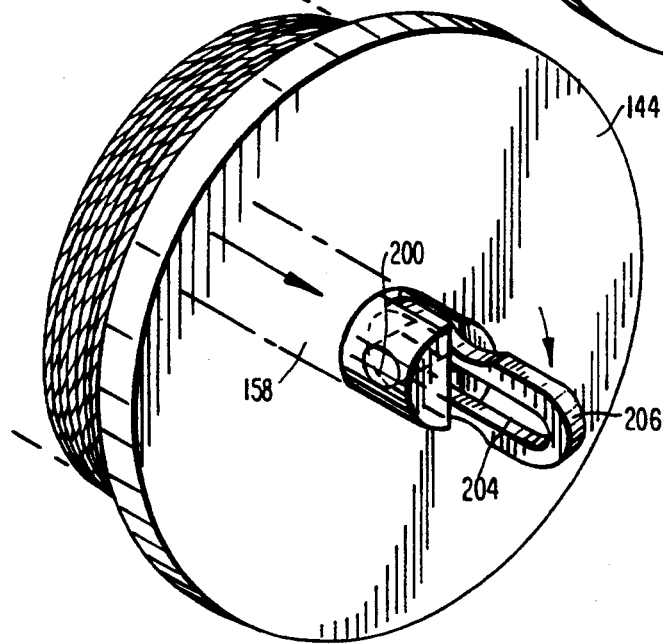
FIG. 16 is a perspective view of the quick-release system of FIG. 15 in the release position.

FIGS. 15 and 16 illustrate the quick connect/quick release feature utilized to retain the take-up spool 144 on shaft 158 shown in FIG. 13. Shaft 158 is dimensioned to receive pin 200 and includes a groove 202. A generally endless looped lock member having a cut-out portion 204 shaped to receive pin 200 is positioned within the slot and is rotatable from a position transverse of the shaft 158 as shown in FIG. 15, to a position in alignment with shaft 158 as shown in FIG. 16. The position of lock member 206 shown in FIG. 15 retains the spool 144 on shaft 158 and is secured in position by appropriately dimensioning space 202 relative to pin 200. The position of lock member 206 shown in FIG. 16 permits ready removal of the take-up spool 144 for replacement with an empty spool. Thus, the quick release feature of lock member 206 facilitates ready replacement of a full spool 144. As shown in FIG. 13, member 144c is fixed to shaft 158 by pin 144d. Pin in slot engagement of pin 144a in slot 144b restrains spool 144 mounted on shaft 158 against rotation relative to shaft 158.

Figure 19:
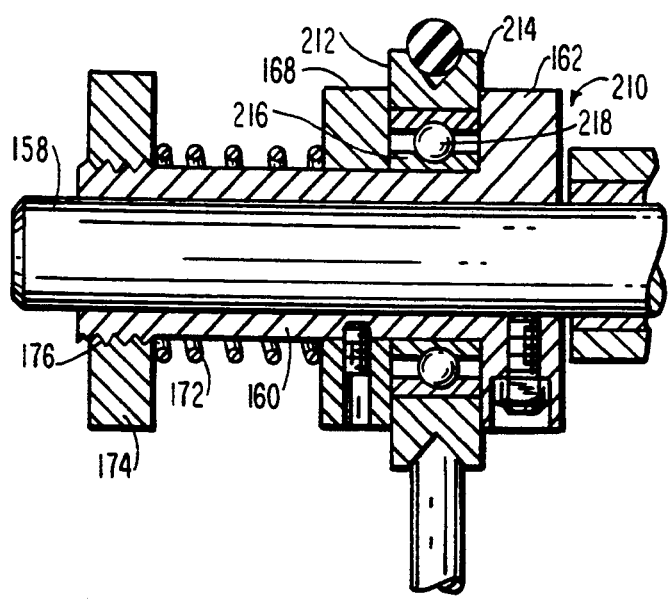
FIG. 19 is a cross-sectional view of an alternative take-up clutch construction for controlling take-up tension on the finished braided suture.
Figure 20:
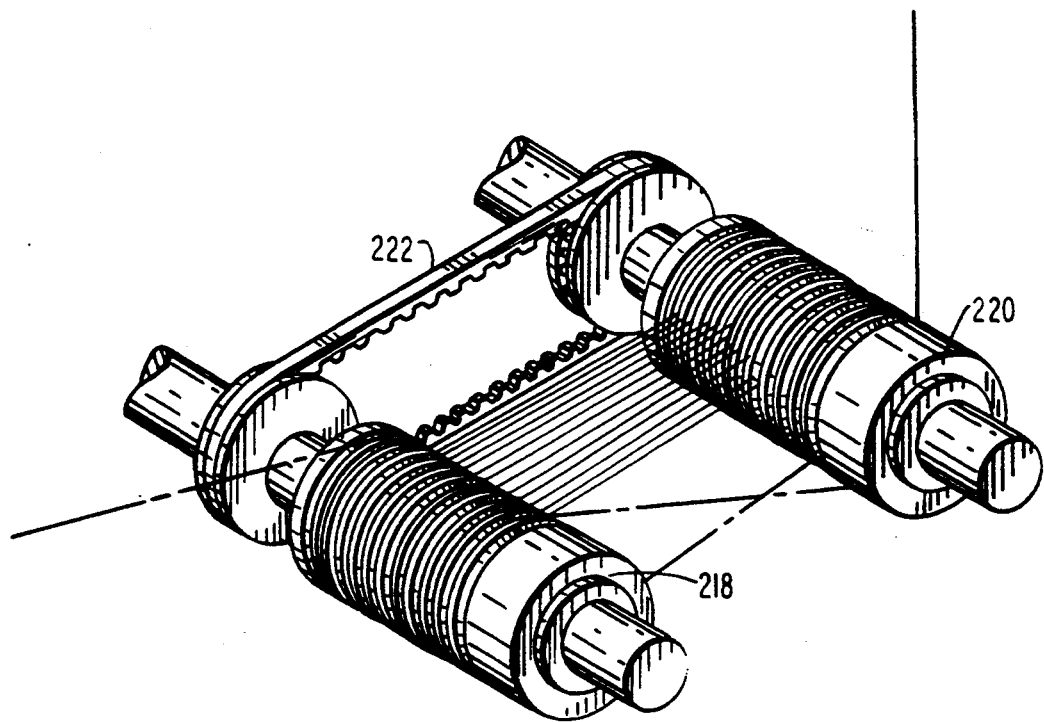
FIG. 20 is a perspective view of an alternate embodiment of the suture take-up rollers of the invention in horizontal tandem positions.

Referring to FIG. 19, an alternate construction of a tensioning take-up clutch is illustrated at 210. Clutch 210 is operative similar to the clutch 156 described previously, but includes split pulley 212 having an outer annular portion 214 and inner portion 216 separated by ball bearings 218. Thus, the construction shown permits precise control over the tension exerted on split member 214 by frictional engagement with members 162, 168 independently of friction between split member 216 and clutch shaft 160. The foregoing alternative structure facilitates improved accuracy in the control of the tension exerted on the final braided suture. FIG. 20 illustrates an alternate arrangement for tensioning and take-up rollers 146, 148. In the arrangement shown, rollers 218, 220 are positioned longitudinally and driven by common belt drive 222. Finished braided suture product 5 is shown. Configuring the take-up rollers in this open-ended configuration facilitates winding of suture material onto the rollers in setting up the apparatus for braiding.

It will be readily appreciated that the features of the present invention as described hereinabove make it possible to produce a fine denier braid capable of application as a suture for surgery. More particularly, the braiding apparatus is well suited for high speed production of consistently high quality final braided suture products having an overall suture denier ranging from as low as about 50 denier to as large as about 4,000 denier. Core yarns will have a preferred denier of from as low as about 20 denier to as high as about 2,400 denier, and sheath yarns will have a denier of from as low as about 0.2 denier to as high as about 6.0 denier.

What is claimed is:

1. An apparatus for braiding yarns comprising:
    a frame;
    a plurality of yarn bobbin carriers movably mounted on said frame, each said yarn bobbin carrier including an upright spindle for supporting a bobbin and a support member in adjacent relationship with said upright spindle for supporting a bobbin for dispensing yarn toward a braiding zone, said upright spindle having a generally tapered spindle tip portion and a grooved portion;
    a substantially planar bobbin securement member made of a resilient material, said bobbin securement member attached to each said support member and having a pair of legs spaced apart from each other and configured and dimensioned to receive therebetween a portion of said spindle extending above said bobbin; and
    means for hingedly supporting each said bobbin securement member to provide pivotal movement thereof between a first upright position substantially parallel to said spindle whereby said legs are disengaged from said spindle, to a second position whereby said legs of said bobbin securement member engage said grooved portion of said spindle tip portion of said spindle above said bobbin.

2. The apparatus of claim 1 wherein said means for hingedly supporting each said bobbin securement member comprises at least one aperture formed in said bobbin securement member and at least one corresponding aperture formed in said support member, said apertures in general alignment to receive a hinge pin therethrough.

3. The apparatus of claim 2, wherein said legs define an opening therebetween for reception of said spindle.

4. The apparatus of claim 3 wherein said leg portions are constructed of a resilient plastic material.

5. The apparatus of claim 4 wherein said grooved portion of said spindle is generally circumferential.

6. The apparatus of claim 5 wherein said tip portion of said spindle has a frusto-conical region.

7. A braider bobbin carrier comprising:
   a carrier housing;
   a spindle extending from said carrier housing and configured and dimensioned to receive a yarn bobbin mounted thereupon, said spindle having an upper spindle tip portion having a substantially frusto-conical shaped portion and a circumferential recess between said frusto-conical shaped portion and said carrier housing;
   a securement support extending from said carrier housing substantially parallel to said spindle; and
   a substantially planar bobbin securement member bingedly attached to said securement support, said bobbin securement member having a pair of legs spaced apart from each other and configured and dimensioned to engageably receive therebetween said upper spindle tip portion of said spindle, said bobbin securement member movable between a bobbin securing position in which said upper spindle tip portion of said spindle extends between said legs in engagement therewith, and an upright bobbin release position substantially parallel to said spindle disengaged from said upper spindle tip portion.

8. The braider bobbin carrier of claim 7 further comprising yarn guide means movably mounted to said securement support.

9. The braider bobbin carrier of claim 8 further comprising bobbin positioning means for selectively preventing rotation of said bobbin about said spindle, said bobbin positioning means movable in response to movement of said yarn guide means between a first position for preventing said bobbin from rotating on said carrier about said spindle and a second position permitting rotation of said bobbin.

10. The braider bobbin carrier of claim 9 wherein said frusto-conical shaped portion has a minor diameter relatively distal to said carrier housing and a major diameter relatively proximal to said carrier housing.

11. The braider bobbin carrier of claim 10 wherein said major diameter is approximately equal to the diameter of said spindle.

12. The braider bobbin carrier of claim 10 wherein said recess is defined by inclined surfaces, distal and proximal relative to said carrier housing.

13. The braider bobbin carrier of claim 12 wherein said inclined distal and proximal surfaces define an included angle of about 90°.

14. The braider bobbin carrier of claim 12 wherein said bobbin securement member comprises a substantially planar base portion and said legs extend longitudinally from said substantially planar base portion.

15. The braider bobbin carrier of claim 14 further comprising means for hingedly securing said base portion to said securement support.

16. The braider bobbin carrier of claim 15 wherein said legs define an opening therebetween for receiving said spindle tip portion.

17. The braider bobbin carrier of claim 16 wherein said legs are constructed of a resilient plastic material.

18. The braider bobbin carrier of claim 16 wherein said legs are disposed in said circumferential recess of said spindle when said bobbin securement member is in said bobbin securing position, and wherein said legs are released from said spindle tip portion when said bobbin securement means is in said bobbin release position.

19. The braider bobbin carrier or claim 18 wherein said legs are spaced apart letter than an outer dimension of said spindle tip portion so as to be forced apart by said spindle tip portion as said bobbin securement member moves from said bobbin release position to said bobbin securing position, said legs being formed of a resilient material to resiliently engage said recess when said bobbin securement member is in said bobbin securing position.

20. The braider bobbin carrier of claim 9 wherein a bobbin is mounted on each yarn bobbin carrier and each said bobbin includes a substantially cylindrical opening along the longitudinal axis thereof to receive said spindle.

21. The braider bobbin carrier of claim 20 wherein said bobbin has a segmented portion selectively engageable with said bobbin positioning means.

22. The braider bobbin carrier of claim 7 wherein said spaced apart pair of legs of said substantially planar bobbin securement member define a spindle engaging recess dimensioned such that engagement between said bobbin securement member and said upper spindle tip portion occurs when said bobbin securement member is moved to said bobbin securing position and said upper spindle tip portion is received within said recess.

23. The braider bobbin carrier of claim 22 wherein said spaced apart pair of legs are resiliently movable away from each other to cammingly receive said upper spindle tip portion within said recess and resiliently movable toward each other to provide cammed engagement with said circumferential recess of said spindle tip portion to secure said bobbin in position on said spindle.

24. The braider bobbin carrier of claim 23 wherein said substantially planar bobbin securement member is formed of a resilient material and said pair of spaced apart legs are monolithic therewith.

25. The braider bobbin carrier of claim 24 wherein said spaced apart pair of legs each have a tapered shape and said spindle tip portion engaging recess is disposed in a region of said legs of greater thickness than a remaining portion wherein structural support is provided to facilitate said camming engagement between said bobbin securement member and said spindle tip portion.

26. The braider bobbin carrier of claim 25 wherein said spaced apart pair of legs have a cross-sectional configuration in the region defining said spindle tip portion engaging recess which is substantially complementary to said circumferential recess in said spindle tip portion to facilitate said camming engagement between said pair of legs and said upper spindle tip portion when said substantially planar bobbin securement member is moved to said bobbin securement position.

27. An apparatus for braiding fine denier yarns to form a braided suture product which comprises:
   a) a frame;
   b) a plurality of yarn carriers associated width said frame for supporting a plurality of bobbins containing fine denier yarns, each said yarn carrier having an upright spindle to receive a bobbin mounted thereupon each said upright spindle having an upper tip portion of frusto-conical configuration extending above said bobbin, and a circumferential recess positioned between said upper tip portion and said yarn carrier;
   c) a yarn guide support in adjacent relationship with said upright spindle;
   d) means for directing said plurality of yarn carriers and said bobbins through predetermined paths while dispensing yarn from each bobbin toward a common braiding zone to form an elongated braid construction;

28. The apparatus for braiding fine denier yarns of claim 27 wherein a bobbin is supported on each yarn bobbin carrier and each said bobbin is rotatable on said yarn carrier for dispensing yarns to said braiding zone, and each said yarn carrier includes means for selectively preventing rotation of said bobbin and for selectively permitting rotation of said bobbin in dependence on the tension in the yarn.

29. The apparatus for braiding fine denier yarns of claim 28 wherein each said individual yarn carrier comprises a pivotal arm having yarn guide means for guiding yarn from said bobbin to said braiding zone.

30. The apparatus for braiding fine denier yarns of claim 29 wherein each said bobbin contains a plurality of radially extending segments positioned at least about a lower surface of said bobbin.

31. The apparatus for braiding fine denier yarns according to claim 30 wherein said pivotal arm is connected to an upstanding pawl arranged to enter into a space defined between said radial segments on each said bobbin in dependence upon the tension in the yarn so as to prevent rotation of said bobbin in dependence upon the tension in the yarn and to permit withdrawal of said pawl from said space when the yarn tension exceeds a predetermined value.

32. The apparatus for braiding fine denier yarns of claim 31 wherein resilient means provided to bias said pivotal arm against pivotal movement which causes withdrawal of said pawl from a space between said segments on said bobbin when the tension in the yarn exceeds about 7 grams.

33. The apparatus for braiding fine denier yarns of claim 32 wherein said resilient means is a coil spring arranged to bias one end portion of said pivotal arm to cause said upstanding pawl to enter into a said radial segments when the tension in the yarn goes below about 5 grams.

34. The apparatus for braiding fine denier yarns of claim 33 wherein said coil spring has a spring rate of from 0.6 to 0.7 pounds per inch.

35. The apparatus for braiding fine denier yarns of claim 34 wherein said yarn is arranged to be dispensed from said bobbin and to extend to said yarn guide means on said carrier in a manner to lift one end of said pivotal arm when the yarn tension exceeds a predetermined value of 7 grams so as to cause withdrawal of said pawl from said space defined by said radial segments on said bobbin thereby permitting rotation of said bobbin as the yarn is drawn therefrom by the tension produced at said braiding zone.

36. The apparatus for braiding fine denier yarns of claim 35 wherein said quick release means comprises a base portion and two resilient legs extending longitudinally from said base portion, said leg portions including adjacent arcuate sections which define an opening therebetween for reception of an upper portion of said spindle to retainably mount said bobbin on said spindle.

37. The apparatus for braiding fine denier yarns of claim 36 wherein said upper portion of said spindle includes a circumferential recess extending entirely thereabout, said recess correspondingly configured and dimensioned to be engaged by said arcuate sections of said leg portions.

38. The apparatus for braiding fine denier yarns of claim 37 wherein said spindle defines a longitudinal axis and said circumferential recess comprises a pair of adjacent surfaces inclined with respect to said longitudinal axis and inclined opposite with respect to each other.

39. The apparatus for braiding fine denier yarns of claim 38 further comprising means for pivotally securing said bobbin securement means to allow for pivotal movement of said base portion from a generally horizontal spindle engaging position to a generally vertical non-engaging position.

* * * * *